US005166381A

United States Patent [19]

Teuscher et al.

[11] Patent Number: 5,166,381

[45] Date of Patent: Nov. 24, 1992

[54] BLOCKING LAYER FOR PHOTORECEPTORS

[75] Inventors: Leon A. Teuscher; Ronald F. Ziolo, both of Webster, N.Y.

[73] Assignee: Xerox Corporation, Stamford, Conn.

[21] Appl. No.: 776,445

[22] Filed: Oct. 17, 1991

Related U.S. Application Data

[62] Division of Ser. No. 575,610, Aug. 31, 1990.

[51] Int. Cl.$^5$ .......................... C07C 1/00; C07C 1/08; C07C 3/00; C07C 7/00

[52] U.S. Cl. ...................................... 556/110; 556/42; 556/45; 556/51; 556/57; 556/118; 556/136; 556/138

[58] Field of Search ................... 556/110, 118, 42, 45, 556/51, 57, 136, 138

[56] References Cited

U.S. PATENT DOCUMENTS

| | | | |
|---|---|---|---|
| 3,121,006 | 2/1964 | Middleton et al. | 430/58 X |
| 3,357,989 | 12/1967 | Byrne et al. | 430/59 |
| 3,442,781 | 5/1969 | Weinberger | 430/59 |
| 4,265,990 | 5/1981 | Stolka et al. | 430/59 |
| 4,286,033 | 8/1981 | Neyhart et al. | 430/58 |
| 4,291,110 | 9/1981 | Lee | 430/59 |
| 4,338,387 | 7/1982 | Hewitt | 430/58 |
| 4,415,639 | 11/1983 | Horgan | 430/57 |
| 4,464,450 | 8/1984 | Teuscher | 430/59 |
| 4,599,286 | 7/1986 | Limburg et al. | 430/59 |
| 4,639,401 | 1/1987 | Mishra et al. | 429/30 |
| 4,654,284 | 3/1987 | Yu et al. | 430/59 |
| 4,664,995 | 5/1987 | Horgan et al. | 430/59 |
| 4,678,844 | 7/1987 | Sakuragi | 525/417 |
| 4,725,518 | 2/1988 | Carmichael et al. | 430/58 |
| 4,786,570 | 11/1988 | Yu et al. | 430/58 |

FOREIGN PATENT DOCUMENTS

| | | |
|---|---|---|
| 0289216 | 11/1988 | European Pat. Off. . |
| 0295125 | 12/1988 | European Pat. Off. . |
| 58-132751 | 8/1983 | Japan . |
| 2097414 | 11/1982 | United Kingdom . |

*Primary Examiner*—Arthur C. Prescott
*Attorney, Agent, or Firm*—Oliff & Berridge

[57] ABSTRACT

Charge blocking materials include a complex or salt of a film forming material containing at least one nitrogen-containing compound, such as an amino, an imino or a tertiary amine group, chelated to a metal ion or atom. The charge blocking materials may be used in a charge blocking layer of an electrophotographic imaging member. The charge blocking materials may be used with transparent conductive layers, for example, comprising cuprous iodide.

8 Claims, 1 Drawing Sheet

BLOCKING LAYER FOR PHOTORECEPTORS

This is a division of application Ser. No. 07/575,610 filed Aug. 31, 1990.

BACKGROUND OF THE INVENTION

This invention relates in general to electrophotography and, in particular, to an electrophotographic imaging member.

In electrophotography, an electrophotographic plate containing a photoconductive insulating layer on a conductive layer is imaged by first uniformly electrostatically charging its surface. The plate is then exposed to a pattern of activating electromagnetic radiation such as light. The radiation selectively dissipates the charge in the illuminated areas of the photoconductive insulating layer while leaving behind an electrostatic latent image in the non-illuminated areas. This electrostatic latent image may then be developed to form a visible image by depositing finely divided electroscopic marking particles on the surface of the photoconductive insulating layer. The resulting visible image may then be transferred from the electrophotographic plate to a support such as paper. This imaging process may be repeated many times with reusable photoconductive insulating layers.

An electrophotographic imaging member may be provided in a number of forms. For example, the imaging member may be a homogeneous layer of a single material such as vitreous selenium or it may be a composite layer containing a photoconductor and another material. One type of composite imaging member comprises a layer of finely divided particles of a photoconductive inorganic compound dispersed in an electrically insulating organic resin binder. U.S. Pat. No. 4,265,990 discloses a layered photoreceptor having separate photogenerating and charge transport layers. The photogenerating layer is capable of photogenerating holes and injecting the photogenerated holes into the charge transport layer.

As more advanced, higher speed electrophotographic copiers, duplicators and printers were developed, degradation of image quality was encountered during extended cycling. Moreover, complex, highly sophisticated duplicating and printing systems operating at very high speeds have placed stringent requirements including narrow operating limits on photoreceptors. For example, the numerous layers found in many modern photoconductive imaging members must be highly flexible, adhere well to adjacent layers, and exhibit predictable electrical characteristics within narrow operating limits to provide excellent toner images over many thousands of cycles. One type of multilayered photoreceptor that has been employed as a belt in electrophotographic imaging systems comprises a substrate, a conductive layer, a blocking layer, an adhesive layer, a charge generating layer, a charge transport layer and a conductive ground strip layer adjacent to one edge of the imaging layers. This photoreceptor may also comprise additional layers such as an anti-curl back coating and an optional overcoating layer.

Multilayered belt photoreceptors tend to delaminate during extended cycling over small diameter support rollers. Alteration of materials in the various belt layers to reduce delamination is not easily effected because the new materials may adversely affect the overall electrical, mechanical and other properties of the belt such as residual voltage, background, dark decay, flexibility, and the like. Problems have been encountered in multilayered photoreceptors in which a substantially transparent photoreceptor is desired. One particular problem is that materials used to obtain a substantially transparent conductive layer, for example, cuprous iodide, do not adhere well to the materials used in the charge blocking layer. Thus, the layers tend to delaminate, resulting in failure of the device.

Another problem is the decrease in conductivity of certain materials used in the conductive layer. The present inventors have discovered that this problem may be associated with the materials used for forming the adjacent charge blocking layer. A number of charge blocking materials are available for forming the charge blocking layer in a photoreceptor. One particularly effective type of material is siloxanes containing nitrogen. Various nitrogen-containing siloxanes are available as charge blocking materials, such as those disclosed in U.S. Pat. Nos. 4,725,518, 4,464,450, 4,599,286, 4,664,995, 4,639,402, and 4,654,284. However, the present inventors have discovered that the conductivity of materials such as cuprous iodide used in the conductive layer is diminished or destroyed by use of blocking layers containing nitrogen-containing siloxanes. A reduction in conductivity of the conductive layer is undesirable as it may result in a total failure of the device.

Accordingly, it is desirable to provide charge blocking materials for a photoreceptor which do not adversely affect the electrical and mechanical properties of the other layers of the device.

SUMMARY OF THE INVENTION

It is an object of the present invention to provide charge blocking materials for a charge blocking layer of an imaging device which do not adversely affect the overall function of the imaging device.

It is another object of the invention to provide charge blocking materials which do not diminish or destroy conductivity of an adjacent conductive layer.

It is also an object of the invention to provide charge blocking materials which exhibit good blocking electrical properties with excellent mechanical properties.

It is another object of the invention to provide a charge blocking layer which has excellent adhesion properties.

It is a further object of the invention to provide a materials combination for a photoreceptor which does not delaminate, and which provides the necessary electrical and mechanical characteristics.

These and other objects of the invention are achieved by providing a charge blocking material comprised of a metal complex or salt of a film forming polymer containing a nitrogen group, such as an amino, an imino and a tertiary amine group. In particular, charge blocking materials are provided wherein the nitrogen-containing group of the charge blocking material is chelated to a metal ion or atom.

BRIEF DESCRIPTION OF THE DRAWINGS

A more complete understanding of the present invention may be obtained by reference to the FIGURE, which is a cross-sectional view of a multilayer photoreceptor of the invention.

DESCRIPTION OF PREFERRED EMBODIMENTS

Figure 1:
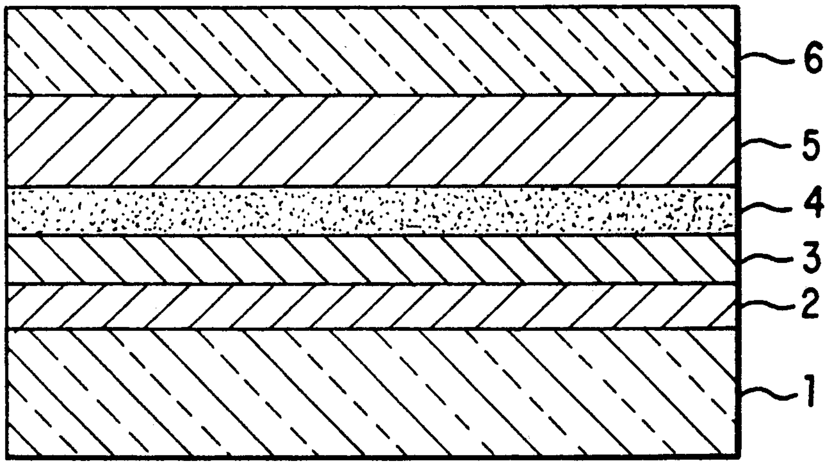

The charge blocking material of the present invention may comprise a metal complex or salt of a film forming polymer containing a nitrogen group, for example an amino, an imino and a tertiary amine group. The metal complexes are formed with a metal ion or atom and the amino, imino or tertiary groups of a charge blocking material. When the charge blocking materials of the invention are used in an imaging device, such as an electroreceptor or a photoreceptor, the material does not adversely affect the properties of adjacent layers, and in particular, an adjacent conductive layer.

A number of charge blocking materials contain nitrogen, and in particular amino, imino, or tertiary amine groups. The present inventors have discovered that these groups may react with materials in an adjacent layer of an imaging member, i.e., the conductive layer. Such interactions have deleterious effects on the properties of the conductive layer and, in particular, reduce or destroy the electrical conductivity of that layer. The present inventors have discovered that this interaction can be prevented by metal-complexing the nitrogen-containing groups of the charge blocking material, thereby rendering innocuous the deleterious effects of these groups.

The charge blocking material of the invention may include any polymer having nitrogen-containing groups such as amino, imino or tertiary amine groups. Examples include polyethyleneimine, n-ethylpolyethyleneimine, and the like, nitrogen-containing siloxanes or nitrogen-containing titanium compounds such as trimethoxysilyl propylene diamine, hydrolyzed trimethoxysilyl propyl ethylene diamine, N-beta-(aminoethyl) and gamma-aminopropyl trimethoxy silane, isopropyl 4-aminobenzene sulfonyl, di(dodecylbenzene sulfonyl) titanate, isopropyl di(4-aminobenzoyl)isostearoyl titanate, isopropyl tri(N-ethylamino-ethylamino)titanate, isopropyl trianthranil titanate, isopropyl tri(N,N-dimethylethylamino)titanate, titanium-4-amino benzene sulfonte oxyacetate, titanium 4-aminobenzoate isostearate oxyacetate, $[H_2N(CH_2)_4]CH_3Si(OCH_3)_2$ (gamma-aminobutyl) methyl diethoxysilane, $[H_2N(CH_2)_3]CH_3Si(OCH_3)_2$ (gamma-aminopropyl) methyl diethoxysilane, as disclosed in U.S. Pat. Nos. 4,338,387, 4,286,033 and 4,291,110. The complexing material may be any material capable of complexing with the nitrogen-containing group of the charge blocking material. The complexing material may be a metal, a metal ion or a metal containing compound. Preferred metals include transition metals, for example, copper, silver, gold, nickel, palladium, platinum, cobalt, rhodium, irridium, iron, ruthenium, osmium, manganese, chromium, vanadium, titanium, zinc, cadmium, mercury, lead, main group metals, and rare earth atoms and the like. Preferably, transition metals are used which coordinate to nitrogen in the charge blocking material. Preferably, transition metals are used which also can form 2, 3, 4, 5 and 6 coordinate species and higher coordination numbers for larger metal ions. The metal ions may be provided in a solution which is added to the hydrolyzed silane solution, and chemically reacted. The resulting solution may then be coated as a charge blocking layer and dried. The dried charge blocking layer is substantially uniform throughout the layer. That is, the layer contains a uniform mixture of the complexed or chelated blocking material.

A preferred hole blocking layer of the invention comprises a reaction product between a hydrolyzed silane containing an amino, imino or tertiary amine group or mixture of hydrolyzed silanes containing an amino, imino or tertiary amine group, and a transition metal. The transition metal complexes with the amino, imino or tertiary amine groups of the silanes, thereby rendering the reactive groups innocuous.

Hydrolyzed silanes have the general formula:

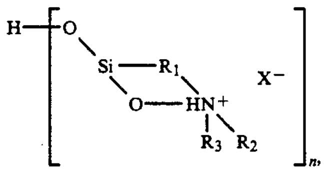

I or

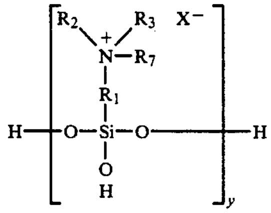

II wherein $R_1$ is an alkylidene group containing 1 to 20 carbon atoms, $R_2$, $R_3$ and $R_7$ are independently selected from the group consisting of H, a lower alkyl group containing 1 to 3 carbon atoms and a phenyl group, X is an anion of an acid or acidic salt, n is 1–4, and y is 1–4.

The hydrolyzed silane may be prepared by hydrolyzing a silane having the following structural formula:

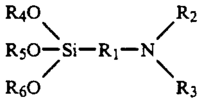

wherein $R_1$ is an alkylidene group containing 1 to 20 carbon atoms, $R_2$ and $R_3$ are independently selected from H, a lower alkyl group containing 1 to 3 carbon atoms, a phenyl group and a poly(ethylene-amino) group, and $R_4$, $R_5$ and $R_6$ are independently selected from a lower alkyl group containing 1 to 4 carbon atoms. Typical hydrolyzable silanes include 3-aminopropyl triethoxy silane, N-aminoethyl-3-aminopropyl trimethoxy silane, 3-aminopropyl trimethoxy silane, (N,N'dimethyl 3-amino) propyl triethoxysilane, N,N-dimethylamino phenyl triethoxy silane, N-phenyl aminopropyl trimethoxy silane, trimethoxy silylpropyldiethylene triamine and mixtures thereof.

If $R_1$ is extended into a long chain, the compound becomes less stable. Silanes in which $R_1$ contains about 3 to about 5 carbon atoms are preferred because the molecule is more stable, is more flexible and is under less strain. Optimum results are achieved when $R_1$ contains 3 carbon atoms. Satisfactory results are achieved when $R_2$ and $R_3$ are alkyl groups. Optimum smooth and uniform films are formed with hydrolyzed silanes in which $R_2$ and $R_3$ are hydrogen. Satisfactory hydrolysis of the silane may be effected when $R_4$, $R_5$ and $R_6$ are alkyl groups containing 1 to 4 carbon atoms. When the alkyl groups exceed 4 carbon atoms, hydrolysis becomes impractically slow. However, hydrolysis of silanes with alkyl groups containing 2 carbon atoms is preferred for best results.

During hydrolysis of the amino silanes described above, the alkoxy groups are replaced with hydroxyl groups. As hydrolysis continues, the hydrolyzed silane takes on the following intermediate general structure:

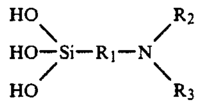

Chemical modification of the reactive amino, imino or tertiary amine groups above with metal ions by complexing or chelating eliminates the detrimental effects of the reactive group.

The hydrolyzed silane solution may be prepared by adding sufficient water to hydrolyze the alkoxy groups attached to the silicon atom to form a solution. Insufficient water will normally cause the hydrolyzed silane to form an undesirable gel. Generally, dilute solutions are preferred for achieving thin coatings. Satisfactory reaction product films may be achieved with solutions containing from about 0.01 percent by weight to about 5 percent by weight of the silane. A solution containing from about 0.05 percent by weight to about 2 percent by weight silane based on the total weight of solution are preferred for stable solutions which form uniform reaction product layers.

Solutions of metal salts, for example acetates, chlorides, bromides, iodides and other soluble species, may be used for the chelation of the reactive amino, imino or tertiary amine groups. Stoichiometric reactions with the nitrogen groups of the blocking material are preferred. For example, ethanol solutions of cupric acetate and 3-aminopropyl triethoxysilane may be prepared to give a 1:4 atom ratio of copper to nitrogen and a water content of about 10% to about 15%. Similarly, metal to nitrogen ratios of 1:2, 1:3, 1:4, 1:5, 1:6 and higher may be used depending on the coordination capacity of the metal and the stereochemistry of the resulting complex. Water content may range from about 5% to about 20%.

Control of the pH of the hydrolyzed silane solution may be effected with any suitable organic or inorganic acid or acidic salt. Typical organic and inorganic acids and acidic salts include acetic acid, citric acid, formic acid, hydrogen iodide, phosphoric acid, ammonium chloride, hydrofluorsilicic acid, bromocresol green, bromophenol blue, p-toluene sulfonic acid and the like.

Any suitable technique may be utilized to apply the blocking layer solution of the invention. Typical application techniques include spraying, dip coating, roll coating, wire wound rod coating, and the like. Hydrolyzed amino silanes complexed with metal described above are preferred.

After drying, the siloxane reaction product film formed from the hydrolyzed silane contains larger molecules which may be linear, partially crosslinked, dimeric, trimeric, or otherwise oligomeric.

Drying or curing of the hydrolyzed silane metal complex upon the conductive layer should be conducted at a temperature greater than about room temperature to provide a reaction product layer having more uniform electrical properties, more complete conversion of the hydrolyzed silane to siloxanes and less unreacted silanol. Generally, a reaction temperature between about 80° C. and about 150° C. is preferred for maximum stabilization of electrical chemical properties. The temperature selected depends to some extent on the specific conductive layer utilized and is limited by the temperature sensitivity of the substrate. Reaction product layers having optimum electrical chemical stability are obtained when reactions are conducted at temperatures of about 120° C. The reaction temperature may be maintained by any suitable technique such as ovens, forced air ovens, radiant heat lamps, microwaves and the like.

The reaction time depends upon the reaction temperatures used. Thus less reaction time is required when higher reaction temperatures are employed. Generally, increasing the reaction time increases the degree of cross-linking of the hydrolyzed silane. Satisfactory results have been achieved with reaction times between about 0.5 minute to about 45 minutes at elevated temperatures. For practical purposes, sufficient cross-linking is achieved by the time the reaction product layer is dry.

The reaction may be conducted under any suitable pressure including atmospheric pressure or in a vacuum. Less heat energy is required when the reaction is conducted at sub-atmospheric pressures.

One may readily determine whether sufficient condensation and cross-linking has occurred to form a siloxane reaction product film having stable electrical chemical properties in a machine environment by merely washing the siloxane reaction product film with water, toluene, tetrahydrofuran, methylene chloride or cyclohexanone and examining the washed siloxane reaction product film to compare infrared absorption of linear or cyclic Si—O— wavelength bands between about 1,000 to about 1,200 $cm^{-1}$. It is believed that the partially polymerized reaction product contains siloxane and silanol moieties in the same molecule. The expression "partially polymerized" is used because total polymerization is normally not achievable even under the most severe drying or curing conditions.

The blocking layers formed from the materials of the present invention do not adversely interact with other layers of an electrophotographic imaging member, as the amino, imino or tertiary amine group is complexed with a metal. For example, the amine group of hydrolyzed gamma-aminopropyl triethoxysilane can be seen to be chelated to copper by the intense blue color of the resulting copper amine complex. Although the amine (or imino or tertiary amine group) is chelated, it is still available as a hole trap against injection. Further, the incorporation of metal such as copper allows for strong adhesion between a conductive layer of cuprous iodide and the blocking layer due to the interaction between the iodine of the copper iodide and the complexed copper. The stability of the blocking layer materials of the invention and the resistance to polymerization may be due to the chelation, and possibly due to zwitterion formation.

A representative structure of an electrophotographic imaging member of the invention is shown in FIG. 1. This imaging member is provided with a supporting substrate 1, an electrically conductive ground plane 2, a charge blocking layer 3 comprising the charge blocking material of the invention, an optional adhesive layer 4, a charge generating layer 5, and a charge transport layer 6. Other layers commonly used in electrophotographic imaging members may also be used, such as anti-curl layers, overcoating layers, and the like.

A description of the layers of the electrophotographic imaging member shown in FIG. 1 follows.

The Supporting Substrate

The supporting substrate may be opaque or substantially transparent and may comprise numerous suitable materials having the required mechanical properties. The substrate may further be provided with an electrically conductive surface. Accordingly, the substrate may comprise a layer of an electrically non-conductive or conductive material such as an inorganic or organic composition. As electrically non-conducting materials, there may be employed various resins known for this purpose including polyesters, polycarbonates, polyamides, polyimides, polyurethanes, and the like. The electrically insulating or conductive substrate can be flexible and may have any number of different configurations such as, for example, a sheet, a scroll, an endless flexible belt, and the like. Preferably, the substrate is in the form of an endless flexible belt and comprises a commercially available biaxially oriented polyester known as Mylar, available from E. I. du Pont de Nemours & Co., or Melinex, available from ICI Americas Inc., or Hostaphan, available from American Hoechst Corporation.

The thickness of the substrate layer depends on numerous factors, including mechanical performance and economic considerations. The thickness of this layer may range from about 65 micrometers to about 150 micrometers, and preferably from about 75 micrometers to about 125 micrometers for optimum flexibility and minimum induced surface bending stress when cycled around small diameter rollers, e.g., 19 millimeter diameter rollers. The substrate for a flexible belt may be of substantial thickness, for example, over 200 micrometers, or of minimum thickness, for example less than 50 micrometers, provided there are no adverse effects on the final photoconductive device. The surface of the substrate layer is preferably cleaned prior to coating to promote greater adhesion of the deposited coating. Cleaning may be effected by exposing the surface of the substrate layer to plasma discharge, ion bombardment, solvent treatment and the like.

The Electrically Conductive Ground Plane

The electrically conductive ground plane may be an electrically conductive metal layer which may be formed, for example, on the substrate by any suitable coating technique, such as a vacuum depositing technique. The conductive layer may comprise cuprous iodide. Cuprous iodide is particularly desirable for a highly transparent conductive layer. The properties of cuprous iodide are not adversely affected when the blocking layer materials of the invention are utilized. When cuprous iodide is used as the conductive layer, it is preferred that an adhesive layer be provided between the cuprous iodide conductive layer and the supporting substrate for improving adhesion.

Other conductive materials such as metals may also be used for the conductive layer. Typical metals include aluminum, copper, gold, zirconium, niobium, tantalum, vanadium, hafnium, titanium, nickel, stainless steel, chromium, tungsten, molybdenum, and the like, and mixtures or alloys thereof.

The conductive layer need not be limited to metals or cuprous iodide. For example, other I-VII semiconductors can be used such as cuprous bromide or chloride, or the corresponding silver salts. Other examples of conductive layers may be combinations of materials such as conductive indium tin oxide as a highly transparent layer for light having a wavelength between about 4000 Angstroms and about 9000 Angstroms or a conductive carbon black dispersed in a plastic binder as a semitransparent or opaque conductive layer.

The conductive layer may vary in thickness over substantially wide ranges depending on the conductivity, optical transparency and flexibility desired for the electrophotoconductive member. Accordingly, for a flexible photoresponsive imaging device, the thickness of the conductive layer may be between about 50 Angstroms to about 1000 Angstroms, and more preferably from about 200 Angstroms to about 800 Angstroms for an optimum combination of electrical conductivity, flexibility and light transmission.

The Blocking Layer

After deposition of the electrically conductive ground plane layer, the blocking layer of the invention may be applied thereto as discussed above in detail. Electron blocking layers for positively charged photoreceptors allow holes from the imaging surface of the photoreceptor to migrate toward the conductive layer. For negatively charged photoreceptors, any suitable hole blocking layer of the invention capable of forming a barrier to prevent hole injection from the conductive layer to the opposite photoconductive layer may be utilized. The thickness of the blocking layer may range from about 20 Angstroms to about 4000 Angstroms, and preferably ranges from about 150 Angstroms to about 2000 Angstroms.

The Adhesive Layer

In most cases, intermediate layers between the blocking layer and the adjacent charge generating or photogenerating layer may be desired to promote adhesion. For example, the adhesive layer 4 may be employed. If such layers are utilized, they preferably have a dry thickness between about 0.001 micrometer to about 0.2 micrometer. Typical adhesive layers include film-forming polymers such as polyester, du Pont 49,000 resin (available from E. I. du Pont de Nemours & Co.), Vitel PE-100 and PE-200 (available from Goodyear Rubber & Tire Co.), polyvinylbutyral, polyvinylpyrrolidone, polyurethane, polymethyl methacrylate, phenoxy resin, and the like.

Du Pont 49,000 is a linear saturated copolyester of four diacids and ethylene glycol having a molecular weight of about 70,000 and a glass transition temperature of 32° C. Its molecular structure is represented as $$HO-\overset{\overset{O}{\|}}{C}-[\text{Diacid-Ethylene glycol}]_{n}OH$$

where n is a number sufficient for achieving the molecular weight of about 70,000. The ratio of diacid to ethylene glycol in the copolyester is 1:1. The diacids are terephthalic acid, isophthalic acid, adipic acid and azelaic acid in a ratio of 4:4:1:1.

Vitel PE-100 is a linear copolyester of two diacids and ethylene glycol having a molecular weight of about 50,000 and a glass transition temperature of 71° C. Its molecular structure is represented as $$HO-\overset{\overset{O}{\|}}{C}-[\text{Diacid-Ethylene glycol}]_{n}OH$$

where n is a number sufficient to achieve the molecular weight of about 50,000. The ratio of diacid to ethylene glycol in the copolyester is 1:1. The two diacids are terephthalic acid and isophthalic acid in a ratio of 3:2.

Vitel PE-200 is a linear saturated copolyester of two diacids and two diols having a molecular weight of about 45,000 and a glass transition temperature of 67° C. The molecular structure is represented as $$HO-\overset{O}{\overset{\|}{C}}-[\text{Diacid-Diol}]_{\overline{n}}OH$$

where n is a number sufficient to achieve the molecular weight of about 45,000. The ratio of diacid to diol in the copolyester is 1:1. The two diacids are terephthalic and isophthalic acid in a ratio of 1.2:1. The two diols are ethylene glycol and 2,2-dimethyl propane diol in a ratio of 1.33:1.

The Charge Generating Layer

Any suitable charge generating (photogenerating) layer may be applied to the adhesive layer 4. Examples of materials for photogenerating layers include inorganic photoconductive particles such as amorphous selenium, trigonal selenium, and selenium alloys selected from the group consisting of selenium-tellurium, selenium-tellurium-arsenic, selenium arsenide; and phthalocyanine pigment such as the X-form of metal-free phthalocyanine described in U.S. Pat. No. 3,357,989; metal phthalocyanines such as vanadyl phthalocyanine and copper phthalocyanine; dibromoanthanthrone; squarylium; quinacridones such as those available from du Pont under the tradenames Monastral Red, Monastral Violet and Monastral Red Y; dibromo anthanthrone pigments such as those available under the trade names Vat orange 1 and Vat orange 3; benzimidazole perylene; substituted 2,4-diamino-triazines disclosed in U.S. Pat. No. 3,442,781; polynuclear aromatic quinones such as those available from Allied Chemical Corporation under the tradenames Indofast Double Scarlet, Indofast Violet Lake B, Indofast Brilliant Scarlet and Indofast Orange; and the like, dispersed in a film forming polymeric binder. Multiphotoegenerating layer compositions may be utilized where a photoconductive layer enhances or reduces the properties of the photogenerating layer. Examples of this type of configuration are described in U.S. Pat. No. 4,415,639. Other suitable photogenerating materials known in the art may also be utilized, if desired. Charge generating layers comprising a photoconductive material such as vanadyl phthalocyanine, metal-free phthalocyanine, benzimidazole perylene, amorphous selenium, trigonal selenium, selenium alloys such as selenium-tellurium, selenium-tellurium-arsenic, selenium arsenide, and the like and mixtures thereof are especially preferred because of their sensitivity to white light. Vanadyl phthalocyanine, metal-free phthalocyanine and tellurium alloys are also preferred because these materials provide the additional benefit of being sensitive to near infrared light.

Any suitable polymeric film-forming binder material may be employed as the matrix in the photogenerating layer. Typical polymeric film-forming materials include those described, for example, in U.S. Pat. No. 3,121,006. The binder polymer should adhere well to the adhesive layer, dissolve in a solvent which also dissolves the upper surface of the adhesive layer and be miscible with the copolyester of the adhesive layer to form a polymer blend zone. Typical solvents include tetrahydrofuran, cyclohexanone, methylene chloride, 1,1,1-trichloroethane, 1,1,2-trichloroethane, trichloroethylene, toluene, and the like, and mixtures thereof. Mixtures of solvents may be utilized to control evaporation range. For example, satisfactory results may be achieved with a tetrahydrofuran to toluene ratio of between about 90:10 and about 10:90 by weight. Generally, the combination of photogenerating pigment, binder polymer and solvent should form uniform dispersions of the photogenerating pigment in the charge generating layer coating composition. Typical combinations include polyvinylcarbazole, trigonal selenium and tetrahydrofuran; phenoxy resin, trigonal selenium and toluene; and polycarbonate resin, vanadyl phthalocyanine and methylene chloride. The solvent for the charge generating layer binder polymer should dissolve the polymer binder utilized in the charge-generating layer and be capable of dispersing the photogenerating pigment particles present in the charge generating layer.

The photogenerating composition or pigment may be present in the resinous binder composition in various amounts. Generally, from about 5 percent by volume to about 90 percent by volume of the photogenerating pigment is dispersed in about 10 percent by volume to about 90 percent by volume of the resinous binder. Preferably from about 20 percent by volume to about 30 percent by volume of the photogenerating pigment is dispersed in about 70 percent by volume to about 80 percent by volume of the resinous binder composition. In one embodiment about 8 percent by volume of the photogenerating pigment is dispersed in about 92 percent by volume of the resinous binder composition.

The photogenerating layer generally ranges in thickness from about 0.1 micrometer to about 5.0 micrometers, preferably from about 0.3 micrometer to about 3 micrometers. The photogenerating layer thickness is related to binder content. Higher binder content compositions generally require thicker layers for photogeneration. Thicknesses outside these ranges can be selected, providing the objectives of the present invention are achieved.

Any suitable and conventional technique may be utilized to mix and thereafter apply the photogenerating layer coating mixture to the previously dried adhesive layer. Typical application techniques include spraying, dip coating, roll coating, wire wound rod coating, and the like. Drying of the deposited coating may be effected by any suitable conventional technique such as oven drying, infrared radiation drying, air drying and the like, to remove substantially all of the solvents utilized in applying the coating.

The Charge Transport Layer

The charge transport layer 6 may comprise any suitable transparent organic polymer or non-polymeric material capable of supporting the injection of photogenerated holes or electrons from the charge generating layer 5 and allowing the transport of these holes or electrons through the organic layer to selectively discharge the surface charge. The charge transport layer not only serves to transport holes or electrons, but also protects the photoconductive layer from abrasion or chemical attack, and therefore extends the operating life of the photoreceptor imaging member. The charge transport layer should exhibit negligible, if any, discharge when exposed to a wavelength of light useful in xerography, e.g. 4000 Angstroms to 9000 Angstroms. The charge transport layer is normally transparent in a wavelength region in which the photoconductor is to be used when exposure is effected therethrough to ensure that most of the incident radiation is utilized by the underlying charge generating layer. When used with a transparent substrate, imagewise exposure or erasure may be accomplished through the substrate with all light passing through the substrate. In this case, the charge transport material need not transmit light in the wavelength region of use. The charge transport layer in conjunction with the charge-generating layer is an insulator to the extent that an electrostatic charge placed on the charge transport layer is not conducted in the absence of illumination.

The charge transport layer may comprise activating compounds or charge transport molecules dispersed in normally electrically inactive film-forming polymeric materials for making these materials electrically active. These charge transport molecules may be added to polymeric materials which are incapable of supporting the injection of photogenerated holes and incapable of allowing the transport of these holes. An especially preferred transport layer employed in multilayer photoconductors comprises from about 25 percent to about 75 percent by weight of at least one charge-transporting aromatic amine, and about 75 percent to about 25 percent by weight of a polymeric film-forming resin in which the aromatic amine is soluble.

The charge transport layer is preferably formed from a mixture comprising at least one aromatic amine compound of the formula:

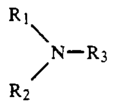

wherein $R_1$ and $R_2$ are each an aromatic group selected from the group consisting of a substituted or unsubstituted phenyl group, naphthyl group, and polyphenyl group and $R_3$ is selected from the group consisting of a substituted or unsubstituted aryl group, an alkyl group having from 1 to 18 carbon atoms and a cycloaliphatic group having from 3 to 18 carbon atoms. The substituents should be free from electron-withdrawing groups such as $NO_2$ groups, CN groups, and the like. Typical aromatic amine compounds that are represented by this structural formula include:

I. Triphenyl amines such as:

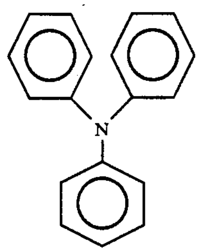

II. Bis and poly triarylamines such as:

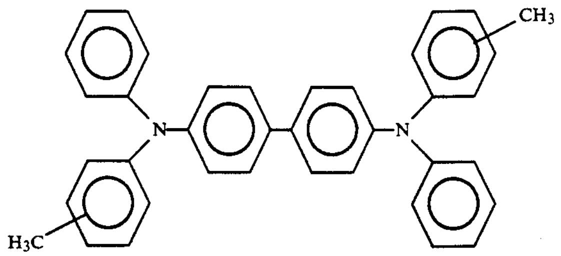

III. Bis arylamine ethers such as:

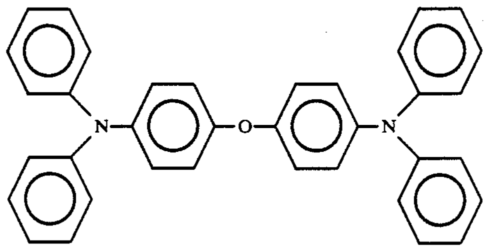

and

IV. Bis alkyl-arylamines such as:

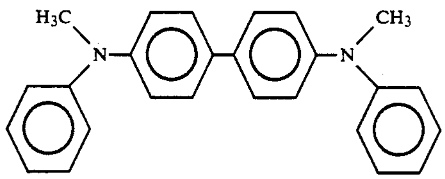

A preferred aromatic amine compound has the general formula:

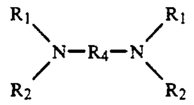

wherein $R_1$ and $R_2$ are defined above, and $R_4$ is selected from the group consisting of a substituted or unsubstituted biphenyl group, a diphenyl ether group, an alkyl group having from 1 to 18 carbon atoms, and a cycloaliphatic group having from 3 to 12 carbon atoms. The substituents should be free from electron-withdrawing groups such as $NO_2$ groups, CN groups, and the like.

Examples of charge-transporting aromatic amines represented by the structural formulae above include triphenylmethane, bis(4-diethylamine-2-methylphenyl)-phenylmethane; 4-4'-bis(diethylamino)-2,2'-dimethyltriphenylmethane; N,N'-bis(alkylphenyl)-(1,1'-biphenyl)-4,4'-diamine wherein the alkyl is, for example, methyl, ethyl, propyl, n-butyl, etc.; N,N'-diphenyl-N,N'-bis(3-methylphenyl)-(1,1'biphenyl)-4,4'-diamine; and the like, dispersed in an inactive resin binder.

Any suitable inactive resin binder soluble in methylene chloride or other suitable solvents may be employed. Typical inactive resin binders soluble in methylene chloride include polycarbonate resin, polyvinylcarbazole, polyester, polyarylate, polyacrylate, polyether, polysulfone, and the like. Molecular weights can vary from about 20,000 to about 1,500,000. Other solvents that may dissolve these binders include tetrahydrofuran, toluene, trichloroethylene, 1,1,2-trichloroethane, 1,1,1-trichloroethane, and the like.

The preferred electrically inactive resin materials are polycarbonate resins having a molecular weight from about 20,000 to about 120,000, more preferably from about 50,000 to about 100,000. The materials most preferred as the electrically inactive resin material are poly(4,4'-dipropylidene-diphenylene carbonate) with a molecular weight of from about 35,000 to about 40,000, available as Lexan 145 from General Electric Company; poly(4,4'-isopropylidene-diphenylene carbonate) with a molecular weight of from about 40,000 to about 45,000, available as Lexan 141 from General Electric Company; a polycarbonate resin having a molecular weight of from about 50,000 to about 100,000, available as Makrolon from Farbenfabricken Bayer A.G.; a polycarbonate resin having a molecular weight of from about 20,000 to about 50,000, available as Merlon from Mobay Chemical Company; polyether carbonates; and 4,4'-cyclohexylidene diphenyl polycarbonate. Methylene chloride solvent is a desirable component of the charge transport layer coating mixture for adequate dissolving of all the components and for its low boiling point.

An especially preferred multilayer photoconductor comprises a charge-generating layer comprising a binder layer of photoconductive material and a contiguous hole transport layer of a polycarbonate resin material having a molecular weight of from about 20,000 to about 120,000, having dispersed therein from about 25 to about 75 percent by weight of one or more compounds having the formula:

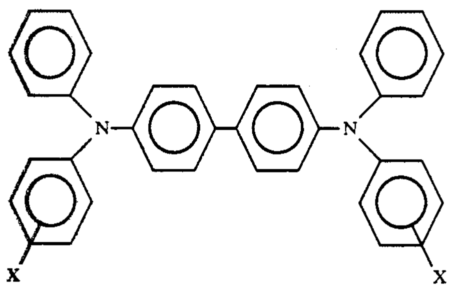

wherein X is selected from the group consisting of an alkyl group, having from 1 to about 4 carbon atoms, and chlorine, the photoconductive layer exhibiting the capability of photogeneration of holes and injection of the holes, the hole transport layer being substantially non-absorbing in the spectral region at which the photoconductive layer generates and injects photogenerated holes but being capable of supporting the injection of photogenerated holes from the photoconductive layer and transporting the holes through the hole transport layer.

The thickness of the charge transport layer may generally range from about 10 micrometers to about 50 micrometers, and preferably from about 20 micrometers to about 35 micrometers. Optimum thicknesses may range from about 23 micrometers to about 31 micrometers.

The invention will further be illustrated with reference to the following, non-limiting examples, it being understood that these examples are intended to be illustrative only, and that the invention is not intended to be limited to the materials, conditions, process parameters and the like recited herein.

COMPARATIVE EXAMPLE I

A solution of 1.2 weight percent of cuprous iodide (CuI) in n-butyronitrile is sprayed upon a blowformed polyester sleeve supported by a rotating mandrel with an automatic spray gun (Binks No. 61). The thickness of this substrate is 4 mils. After drying for 10 minutes at 100° C., the CuI layer is 400 Angstroms thick. This conductive sleeve is cut into three rectangular pieces measuring 9 inches×11 inches.

A charge generating layer is coated on a first piece of 9 inches×11 inches sleeve. About 1.5 grams of a dispersion of 33 volume percent trigonal selenium having a particle size between about 0.05 micron to about 0.20 micron and about 67 volume percent of poly(hydroxyether) resin, Bakelite phenoxy PKHH available from Union Carbide Corporation is added to about 2.5 grams of a solution of tetrahydrofuran containing about 0.025 grams of N,N'-diphenyl-N,N'-bis(3-methylphenyl)1,1'-biphenyl-4,4'-diamine. This mixture is applied with a 0.0005 inch Bird applicator to the CuI layer and the device is then allowed to dry at 135° C. for 3 minutes resulting in the formation of a hole generating layer having a dry thickness of about 0.6 micron containing about 28 volume percent of trigonal selenium dispersed in about 72 volume percent of poly(hydroxyether). The generating layer is then overcoated with a 25 micron thick charge transport layer containing about 50 percent by weight N,N'-diphenyl-N,N'-bis(3-methylphenyl)1,1'-biphenyl-4,4'-diamine dispersed in about 50 percent by weight of polycarbonate resin, Makrolon, available from Bayer Corporation.

The resulting photosensitive member having two electrically operative layers is subjected to electrical negative charging in a xerographic scanner. The results of the scanning test show only an approximately initial 150 volts charge acceptance. This suggests a strong injection of positive charges from the conductive CuI into the electrically active layers.

COMPARATIVE EXAMPLE II

A second device is fabricated using the same procedures as in Example I upon a second piece of cuprous iodide coated polyester with the exception that a blocking layer is coated between the CuI layer and the charge generating layer.

An aqueous 10% water solution is prepared containing about 0.88 percent by weight based on the total weight of the solution (0.004 mole solution), of 3-aminopropyl triethoxysilane. The solution also contains about 95 percent by weight denatured ethanol and about 5 percent by weight isopropanol based on the total weight of the solution (0.004 mole solution). This solution is applied with a 0.0005 inch Bird applicator onto the surface of the CuI coated polyester film and thereafter dried at a temperature of about 135° C. in a forced air oven for about 3 minutes to form a reaction product layer of the partially polymerized silane upon the CuI coated polyester film to form a dried layer having a thickness of about 450 Angstroms measured by infrared reflectance spectrometry and by ellipsometry.

The resulting photosensitive member having two electrically operative layers is subjected to electrical negative charging in a xerographic scanner. The results of scanning show that the device accepts a charge of more than 1000 volts and does not discharge under strong light exposure. This suggests that the silane blocking layer reacts with the CuI layer and destroys its conductivity.

EXAMPLE III

A third device is fabricated as in Comparative Example II upon the third piece of CuI coated polyester with the exception that a blocking layer of the invention is coated between the conductive cuprous iodide layer and the charge generating layer. 1.76 g (0.008 mol) of 3-aminopropyl triethoxysilane is hydrolyzed in 8.24 g of distilled water and 0.002 mol (0.36 g) of anhydrous copper (II) acetate (Aldrich) is dissolved with gentle heating into 86.4 g of 200 proof ethanol. After complete dissolution, this solution is added to the aqueous silane slowly under good stirring. A deep blue color develops. This solution is applied with a 0.0005 inch Bird coater on the surface of the CuI coated polyester film and thereafter dried at a temperature of about 135° C. in a forced air oven for about 3 minutes to form a reaction product layer of the partially polymerized copper (II) modified silane. The layer has a dry thickness of about 1000 Angstroms. The resulting photosensitive device having two electrically operative layers is subjected to electrical cycling in a continuous rotating scanner and shows excellent xerographic properties.

EXAMPLE IV

A blocking layer material is prepared from an ethanol solution of cupric acetate and gamma-amino-propyl triethoxysilane, giving a 1:4 ratio of copper to amine and a water content of 10 to 15% using the same procedures as described in Example III.

A full electrophotographic device is fabricated with the blocking material. In particular, a photoconductive imaging member is prepared by providing a web of CuI (0.06 micron thickness) coated polyester (Melinex) substrate having a thickness of 3 mils, and applying thereto, using a gravure applicator, a solution containing about 2.1 weight percent of the charge blocking layer solution. This layer is then dried for 10 minutes at 135° C. in a forced air oven. The resulting blocking layer has a dry thickness of about 0.1 micrometer.

An adhesive interface layer is then prepared by applying a wet coating containing 49,000 polyester (du Pont) over the blocking layer, using a gravure applicator. The adhesive interface layer is then dried for 10 minutes at 135° C. in a forced air oven. The resulting adhesive interface layer has a dry thickness of 0.05 micrometer.

The adhesive interface layer is thereafter coated with a photogenerating layer containing 7.5 percent by volume trigonal selenium, 25 percent by volume N,N'-diphenyl-N,N'-bis(3-methyl-phenyl)-1,1'-biphenyl-4,4'-diamine, and 67.5 percent by volume polyvinylcarbazole. This photogenerating layer is prepared by introducing 80 grams polyvinylcarbazole to 1400 ml of a 1:1 volume ratio of a mixture of tetrahydrofuran and toluene. To this solution are added 80 grams of trigonal selenium and 10,000 grams of ⅛ inch diameter stainless steel shot. This mixture is then placed on a ball mill for 72 to 96 hours. Subsequently, 500 grams of the resulting slurry are added to a solution of 36 grams of polyvinylcarbazole and 20 grams of N,N'-diphenyl-N,N'-bis(3-methylphenyl)-1,1'-biphenyl-4,4'-diamine in 750 ml of 1:1 volume ratio of tetrahydrofuran/toluene. This slurry is then placed on a shaker for 10 minutes. The resulting slurry is thereafter applied to the adhesive interface with an extrusion die. This photogenerating layer is dried at 135° C. for 5 minutes in a forced air oven to form a photogenerating layer having a dry thickness of 2.3 micrometers.

This member is then coated over with a charge transport layer. The charge transport coating solution is prepared by introducing into a carboy container in a weight ratio of 1:1 N,N'-diphenyl-N,N'-bis(3-methylphenyl)-1,1'-biphenyl-4,4'-diamine, and the binder resin Makrolon 5705, a polycarbonate having a weight average molecular weight from about 50,000 to about 1,000,000, available from Farbenfabricken Bayer AG. The resulting solid mixture is dissolved in methylene chloride to provide a 15 weight percent solution thereof. This solution is then applied onto the photogenerator layer by extrusion coating to form a wet charge transport layer. The resulting photoconductive member is then dried at 135° C. in a forced air oven for 5 minutes to produce a 25 micrometers dry thickness charge transport layer.

The resulting photosensitive device having two electrically operative layers is subjected to electrical testing in a continuous rotating scanner and shows excellent xerographic properties.

EXAMPLE V

The same procedures are followed as described in Comparative Example I except that a blocking solution of silane (0.004 mol) modified by cupric acetate (0.001 mol) in a 85:15 ratio of alcohol (95% ethanol and 5% isopropyl alcohol):water is sprayed with an automatic spray gun (Binks No. 61) upon the electrically conductive cuprous iodide coated sleeve. This sleeve is supported by a rotating mandrel. After spraying, the sleeve is dried at 100° C. for 10 minutes. A charge generating layer is applied from a solution of vanadyl phthalocyanine (80 percent by volume) in Vitel PE-100 polyester (Goodyear) (20 percent by volume) by spraying with an automatic spray gun (Binks No. 61) upon the blocking layer coated sleeve supported by a rotating mandrel. The sprayed layer is dried for one hour at 100° C. and has a dry layer thickness of 0.6 micron. Then a charge transport layer of 40 percent by weight N-N'-diphenyl-N,N'-bis(3-methylphenyl) 1,1'biphenyl diamine in 60 percent by weight bisphenol A-polycarbonate Merlon (Mobay) is sprayed from a solution of 80 parts methylene chloride and 20 parts 1,1,2-trichloroethane with an automatic spray gun (Binks No. 61) in a climatized spray room (18° C./5% RH). After spraying, the device is dried in a forced air oven at 80° C. for 10 minutes, at 100° C. for 10 minutes, and at 120° C. for 10 minutes. The thickness of this layer is 19 microns.

This photoreceptor is evaluated in a rotating xerographic scanner for 50,000 cycles. The scanning results show excellent xerographic properties.

EXAMPLE VI

The same procedures as described in Example III are followed except that the substrate polyester film (Mylar from du Pont) is vacuum coated with 120 Angstroms thickness of titanium in place of the conductive cuprous iodide layer. The resulting photoreceptor exhibits excellent xerographic properties.

EXAMPLE VII

The same procedures are followed as in Example V except that a blocking layer of 0.006 mol 3-aminopropyl triethoxysilane and 0.001 mol cobalt II acetate is used.

The electrical cycling results are the same as those for the photoreceptor of Example V.

EXAMPLE VIII

The same procedures are followed as in Example VI except that the blocking layer is made of 0.002 mol 3-aminopropyl triethoxysilane, 0.002 mol 3-aminopropyl triethoxysilane acetate, and 0.001 mol zinc acetate. The electrical cycling results are very similar to those of Example VI.

While the invention has been described with reference to specific preferred embodiments, it is not intended to be limited thereto. Rather, those skilled in the art will recognize that variations and modifications may be made therein which are within the spirit of the invention and within the scope of the claims.

What is claimed is:

1. A composition, comprised of a complex of a film forming charge blocking polymer containing at least one nitrogen containing group, said polymer being other than an 8-hydroxy quinoline, a dipyridylamine or a cross-linked polyethylene amine, the at least one nitrogen-containing group being chelated to a metal ion or atom.

2. The composition of claim 1, wherein said nitrogen-containing group is selected from the group consisting of amino, imino and tertiary amine.

3. The composition of claim 1, wherein said metal ion or atom is a transition metal.

4. The composition of claim 1, wherein said metal ion or atom is at least one member selected from the group consisting of copper, silver, gold, nickel, palladium, platinum, cobalt, rhodium, irridium, iron ruthenium, osmium, manganese, chromium, vanadium, titanium, zinc, cadmium, mercury and lead.

5. The composition of claim 1, wherein said film forming charge blocking polymer is a silane.

6. The composition of claim 1, wherein said complex is a 3-aminopropyl triethoxysilane metal complex.

7. The composition of claim 1, wherein said complex is a 3-aminopropyl triethoxysilane metal complexed with copper.

8. The composition of claim 1, wherein said polymer is selected from the group consisting of siloxane, silane and titanium polymers.

* * * * *